United States Patent [19]

Böhm et al.

[11] Patent Number: 5,391,811
[45] Date of Patent: Feb. 21, 1995

[54] PROCESS FOR THE PREPARATION OF α-FLUORO-β-DICARBONYL COMPOUNDS

[75] Inventors: Stefan Böhm, Köln; Albrecht Marhold, Leverkusen, both of Germany

[73] Assignee: Bayer Aktiengesellschaft, Leverkusen, Germany

[21] Appl. No.: 147,210

[22] Filed: Nov. 3, 1993

[30] Foreign Application Priority Data

Nov. 10, 1992 [DE] Germany ............................ 4237882

[51] Int. Cl.$^6$ ........................................... C07C 229/00
[52] U.S. Cl. ........................................ 560/43; 560/51; 560/82; 560/172; 560/174; 560/192; 564/155; 564/160; 564/169; 564/199; 564/200; 568/316; 568/394; 568/393
[58] Field of Search ............... 560/43, 51, 82, 172, 560/174, 192; 564/155, 160, 169, 199, 200; 568/316, 394, 393

[56] References Cited

U.S. PATENT DOCUMENTS

| | | | |
|---|---|---|---|
| 3,141,040 | 7/1964 | Inman | 260/558 |
| 3,227,736 | 1/1966 | Tschesche | 260/405.5 |
| 3,480,667 | 11/1969 | Siegart | 260/514 |
| 3,976,691 | 8/1976 | Middleton | 260/544 |
| 5,210,272 | 5/1993 | Palmer | 560/13 |
| 5,254,732 | 10/1993 | Differding | 564/82 |

OTHER PUBLICATIONS

*J. Org. Chem.*, 1989, vol. 54, pp. 5618-5620; "Fluoromalonaldehyde Bis (dialkyl acetals): Synthesis by ... "; Molines et al.

*J. Org. Chem.*, 1991, vol. 56, pp. 273-277; "Acylation of Fluorocarbethoxy Substituted Ylids: A Simple and ... "; Thenappan et al.

*J. Chem. Soc., Chem. Commun.*, 1991, pp. 179-181; "N-Fluoro Perfluoroalkylsulphonimides: Efficient Reagents for ... "; Xu et al.

*Primary Examiner*—Michael L. Shippen
*Attorney, Agent, or Firm*—Sprung Horn Kramer & Woods

[57] ABSTRACT

α-fluoro-β-dicarbonyl compounds are prepared by reacting a halogenated dicarbonyl compound at temperatures of 20° to 100° C. with an addition product of hydrogen fluoride and a trialkylamine. This process is easy to carry out in technical terms and can also be carried out on a large scale.

9 Claims, No Drawings

PROCESS FOR THE PREPARATION OF α-FLUORO-β-DICARBONYL COMPOUNDS

The present invention relates to a process for the preparation of α-fluoro-β-dicarbonyl compounds which is advantageous and is also easy to carry out on the industrial scale.

It is known that ethyl bromofluoroacetate can be reacted with tri-n-butylphosphine to give the corresponding phosphonium salt and that the latter can be converted to the corresponding ylene by reaction with n-butyllithium at −78° C. to give α-fluoro-β-keto-esters by acylation and saponification (see J. Org. Chem. 56, 273–277 (1991)). The disadvantages here are that the starting materials are not readily obtainable, the process has several steps and the required procedure is complicated, e.g. by the handling of phosphines and n-butyllithium, which demand special safety measures and low temperatures.

In another known process, it is possible to prepare α-fluoro-β-dicarbonyl compounds by reacting fluorodichloro-methane with dioxene and subjecting the reaction product to acid-catalysed alcoholysis (see J. Org. Chem. 54, 5618–5620 (1989)). The disadvantages are that the toxic substances fluordichloromethane and dioxene are difficult to handle and that the reaction time required for the saponification is one week.

Finally, it is also known that 1,3-dicarbonyl compounds can be fluorinated regioselectively in the α-position by reaction with N-fluoro-perfluoroalkylsulphonimides (see J. Chem. Soc. Chem. Comm. 1991, 179). The disadvantage of this process is that the sulphonimide required is not easily obtainable.

Thus there is still no process for the preparation of α-fluoro-β-dicarbonyl compounds which can be carried out easily and on the industrial scale.

A process for the preparation of α-fluoro-β-dicarbonyl compounds of formula (I):

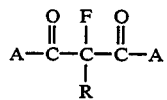
(I)

in which
 the two radicals A can be identical or different and are each alkyl, aryl, alkoxy, aryloxy or an amino group and
 R is hydrogen, fluorine, alkyl or aryl,
has now been found which is characterised in that a dicarbonyl compound of formula (II):

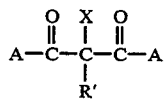
(II)

in which
 X is chlorine, bromine or iodine,
 A is as defined for formula (I) and
 R' is as defined for R in formula (I) and can additionally be chlorine, bromine or iodine, is reacted at temperatures of 20° C. to 100° C. with an addition product of hydrogen fluoride and a trialkylamine.

If R' in the starting material of formula (II) is chlorine, bromine or iodine, an α,α-difluoro-β-dicarbonyl compound is obtained, i.e. a compound of formula (I) in which R is fluorine.

In formulae (I) and (II), A can be for example linear or branched, unsubstituted or substituted alkyl, unsubstituted or substituted aryl, linear or branched, unsubstituted or substituted alkoxy, unsubstituted or substituted aryloxy or an unsubstituted or substituted amino group of formulae (III) to (V):

 (III)

 (IV)

and

 (V)

in which
 $R^1$, $R^2$ and $R^3$ are alkyl, preferably $C_1$–$C_6$-alkyl, or aryl, preferably phenyl, it being possible for $R^2$ and $R^3$ to be identical or different.

The substituents which may be present in the alkyl and alkoxy groups can be for example halogen atoms, preferably fluorine, chlorine and/or bromine, or nitro groups.

The substituents which may be present in the aryl and aryloxy groups can be for example $C_1$–$C_6$-alkyl groups, preferably methyl or ethyl, halogen atoms, preferably fluorine, chlorine and/or bromine, or nitro groups.

As alkyl and alkoxy, A preferably contains 1 to 6 C atoms, especially 1 or 2 C atoms, and as aryl and aryloxy, A is preferably phenyl.

In the formulae (I) and (II), R and R' can be for example hydrogen, linear or branched, unsubstituted or substituted $C_1$–$C_{12}$-alkyl or unsubstituted or substituted phenyl. Examples of suitable substituents for alkyl groups are halogen atoms or nitro groups and examples of suitable substituents for aryl groups are $C_1$–$C_6$-alkyl groups, halogen atoms or nitro groups. In formula (II), R' can additionally be chlorine, bromine or iodine, especially chlorine or bromine.

R and R' are preferably hydrogen.

In formula (II), X is preferably chlorine or bromine.

Some selected examples of dicarbonyl compounds of formula (II) to be used are:

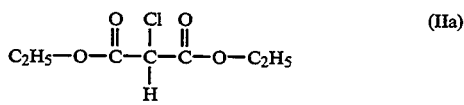 (IIa)

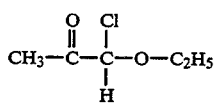 (IIb)

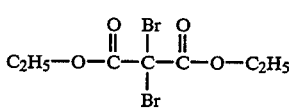 (IIc)

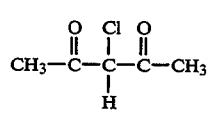 (IId)

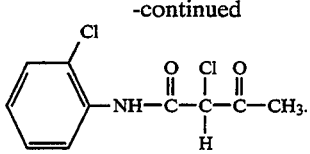

Some selected examples of α-fluoro-β-dicarbonyl compounds of formula (I) which can be prepared according to the invention are:

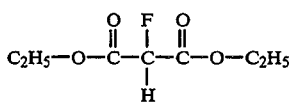

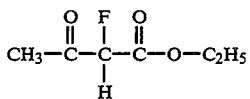

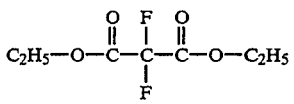

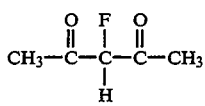

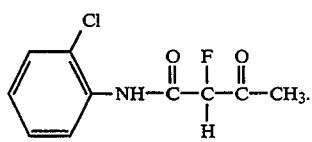

Preferred reaction temperatures for the process according to the invention are in the range 50° C. to 90° C.

Examples of addition products of hydrogen fluoride and trialkylamines can be those containing 1 to 2.8 mol of hydrogen fluoride per mol of trialkylamine. This ratio is preferably 1:1.5 to 2.5 and particularly preferably 1:1.8 to 2.2.

Addition products of 3 mol of hydrogen fluoride and 1 mol of trialkylamine are often readily accessible and can be used to prepare addition products with a lower hydrogen fluoride content, even in situ, by adding the appropriate amount of free trialkylamine.

Examples of suitable trialkylamines are those containing identical or different alkyl groups each having 1 to 6 C atoms. They preferably contain three identical alkyl groups. Triethylamine is particularly preferred.

Addition products of hydrogen fluoride and trialkylamine can be used in amounts of 1 to 4 mol, for example, based on dicarbonyl compounds of formula (II). It is preferable to use 1 to 3 mol of addition product per mol of dicarbonyl compound of formula (II).

The process according to the invention can be carried out in the presence or absence of a solvent, examples of suitable solvents being nitriles, especially acetonitrile, dialkylamides, especially dimethylformamide, and chlorinated hydrocarbons, especially methylene chloride.

The mixture obtained after the reaction can be worked up for example by a procedure in which any solvent present is first stripped off under vacuum, the mixture is then discharged into water and extracted with a water-immiscible organic solvent, e.g. with methylene chloride, and the α-fluoro-β-dicarbonyl compound of formula (I) prepared is finally isolated from the organic phase by fractionation.

The process according to the invention is distinguished by a number of advantages. It only requires readily accessible starting materials and auxiliaries, most of which are commercially available, α-fluoro-β-dicarbonyl compounds of formula (I) are obtained easily and in good yields, and no special measures are required for handling particularly toxic substances.

α-Fluoro-β-dicarbonyl compounds of formula (I) are important intermediates, for example for the preparation of α-fluoroacrylic acid esters by the process described in European patent application A-203 462. α-fluoroacrylic acid esters can be used to prepare high-molecular non-crystalline polymers which are transparent and have softening points above 100° C.

EXAMPLE 1

195 g of diethyl chloromalonate were dissolved in 500 ml of acetonitrile, and 320 g of the addition product of 3 mol of hydrogen fluoride and 1 mol of triethylamine were added in the absence of moisture. 100 g of triethylamine were then added and the mixture was stirred at an internal temperature of 80° C. until conversion was complete. The solvent was then distilled off and the residue was poured into water. The diethyl fluoromalonate of formula (Ia) obtained was extracted with methylene chloride and the extract was washed with saturated aqueous sodium hydrogencarbonate solution, dried over magnesium sulphate and fractionated under high vacuum. The yield was 147 g=83% of theory.

EXAMPLE 2

165 g of ethyl chloroacetoacetate were dissolved in 500 ml of acetonitrile, and 320 g of the addition product of 3 mol of hydrogen fluoride and 1 mol of triethylamine were added in the absence of moisture. 100 g of triethylamine were then added and the mixture was stirred at an internal temperature of 80° C. until conversion was complete. The solvent was then distilled off, the residue was poured into water, the ethyl fluoroacetoacetate of formula (Ib) obtained was extracted with methylene chloride and the extract was washed with saturated aqueous sodium hydrogencarbonate solution, dried over magnesium sulphate and fractionated under high vacuum. The yield was 96 g=65% of theory.

EXAMPLE 3

480 g of the addition product of 3 mol of hydrogen fluoride and 1 mol of triethylamine were added to 243 g of diethyl 2,2-dibromomalonate, 150 g of triethylamine were then added and the mixture was stirred at an internal temperature of 70° C. until conversion was complete according to GC. The reaction mixture was then cooled and poured into water. The product of formula (Ic) was extracted with methylene chloride and the extract was washed with saturated aqueous sodium hydrogencarbonate solution, dried over magnesium sulphate and distilled under vacuum to give 108 g (=72% of theory) of diethyl 2,2-difluoromalonate with a boiling point of 78° -80° C. at 10 mbar.

EXAMPLE 4

134.6 g of 3-chloropentane-2,4-dione were dissolved in 500 ml of acetonitrile, and 320 g of the addition product of 3 mol of hydrogen fluoride and 1 mol of triethylamine were added in the absence of moisture. 100 g of triethylamine were then added and the mixture was stirred at an internal temperature of 80° C. until conversion was complete. 400 ml of solvent were then distilled off and the residue was poured into water. The product was extracted with methylene chloride and the extract was washed with saturated aqueous sodium hydrogencarbonate solution, dried over magnesium sulphate and fractionated under vacuum to give 38 g (=32% of theory) of 3-fluoropentane-2,4-dione (formula (Id)) with a boiling point of 88° C. at 30 mbar.

EXAMPLE 5

25 g of 2-chloro-acetoacetic acid ortho-chloroanilide were dissolved in 75 ml of acetonitrile, and 32 g of the addition product of 3 mol of hydrogen fluoride and 1 mol of triethylamine were added in the absence of moisture. 10 g of triethylamine were then added and the mixture was stirred at an internal temperature of 80° C. until conversion was complete. 60 ml of solvent were then distilled off and the residue was poured into water. The product was extracted with methylene chloride and the extract was washed with saturated aqueous sodium hydrogencarbonate solution, dried over magnesium sulphate and concentrated on a rotary evaporater. The product was purified by chromatography on silica gel using methylene chloride as the eluent to give 15.8 g (=69% of theory) of 2-fluoro-acetoacetic acid ortho-chloroanilide of formula (Ie).

What is claimed is:

1. A process for the preparation of α-fluoro-β-dicarbonyl compounds of formula (I)

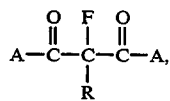

in which
the two radicals A are identical or different and each represents alkyl, aryl, alkoxy, aryloxy or an amino group and
R represents hydrogen, fluorine, alkyl or aryl,
in which process a dicarbonyl compound of formula (II)

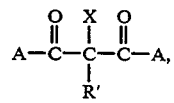

in which
X represents chlorine, bromine or iodine, A is as defined for in formula (I) and R' is as defined for R in formula (I) and can additionally represent chlorine, bromine or iodine,
is reacted at temperatures of 20° C. to 100° C. with an addition product of hydrogen fluoride and a trialkylamine.

2. The process of claim 1, in which in formulae (I) and (II), A represents linear or branched, unsubstituted or substituted alkyl, unsubstituted or substituted aryl, linear or branched, unsubstituted or substituted alkoxy, unsubstituted or substituted aryloxy or an unsubstituted or substituted amino group of formulae (III) to (V)

$$NH_2, \quad (III)$$

$$NHR^1 \quad (IV)$$

and $$NR^2R^3, \quad (V)$$

in which
$R^1$, $R^2$ and $R^3$ represent alkyl or aryl and $R^2$ and $R^3$ can be identical or different.

3. The process of claim 1, in which A as alkyl and alkoxy contains 1 to 6 C atoms or A is phenyl.

4. The process of claim 1, in which in formulae (I) and (II), R and R' represent hydrogen, linear or branched, unsubstituted or substituted $C_1$–$C_{12}$-alkyl or unsubstituted or substituted phenyl, and R' can additionally represent chlorine, bromine or iodine.

5. The process of claim 1, in which in formulae (I) and (II), R and R' represent hydrogen.

6. The process of claim 1, in which the addition product of hydrogen fluoride and a trialkylamine contains 1 to 2.8 mol of hydrogen fluoride per mol of trialkylamine.

7. The process of claim 1, in which the trialkylamine is triethylamine.

8. The process of claim 1, in which from 1 to 4 mol of the addition product of hydrogen, fluoride and trialkylamine are used, based on the dicarbonyl compound of formula (II).

9. The process of claim 1, which is carried out at temperatures in the range 50° to 90° C.

* * * * *